(12) United States Patent
Dallas et al.

(10) Patent No.: US 8,984,945 B2
(45) Date of Patent: Mar. 24, 2015

(54) SYSTEM AND DEVICE FOR ACOUSTIC MEASURING IN A MEDIUM

(75) Inventors: James Dallas, Superior, CO (US); Frans Lautzenhiser, Zionsville, IN (US); Eric Molz, Houston, TX (US)

(73) Assignee: PiezoTech LLC, Indianapolis, IN (US)

( * ) Notice: Subject to any disclaimer, the term of this patent is extended or adjusted under 35 U.S.C. 154(b) by 0 days.

(21) Appl. No.: 14/136,144

(22) PCT Filed: Jun. 22, 2012

(86) PCT No.: PCT/US2012/043755
§ 371 (c)(1),
(2), (4) Date: Dec. 20, 2013

(87) PCT Pub. No.: WO2012/178013
PCT Pub. Date: Dec. 27, 2012

(65) Prior Publication Data
US 2014/0219057 A1    Aug. 7, 2014

Related U.S. Application Data

(60) Provisional application No. 61/499,809, filed on Jun. 22, 2011.

(51) Int. Cl.
| G01N 29/07 | (2006.01) |
| G01V 1/40 | (2006.01) |
| E21B 47/10 | (2012.01) |

(52) U.S. Cl.
CPC ...... G01N 29/07 (2013.01); G01V 1/40 (2013.01); E21B 47/101 (2013.01)
USPC ............................................. 73/597; 367/86

(58) Field of Classification Search
USPC ........ 73/597, 152.02, 152.08, 152.18; 367/86
See application file for complete search history.

(56) References Cited

U.S. PATENT DOCUMENTS

| 4,208,966 | A | * | 6/1980 | Hart ............................... 102/310 |
| 4,452,077 | A | | 6/1984 | Siegfried |
| 4,532,812 | A | | 8/1985 | Birchak |
| 4,709,357 | A | | 11/1987 | Maki, Jr. |
| 4,905,203 | A | | 2/1990 | Sims et al. |
| 4,982,383 | A | | 1/1991 | Sims et al. |
| 5,031,155 | A | | 7/1991 | Hsu |
| 5,044,462 | A | | 9/1991 | Maki, Jr. |

(Continued)

*Primary Examiner* — J M Saint Surin
(74) *Attorney, Agent, or Firm* — Overhauser Law Offices LLC

(57) ABSTRACT

A device for acoustic measuring in a medium in a borehole such as velocity of sound in the medium or velocity of the medium, includes at least a first acoustic array situated in a first, slanted sidewall of a measuring area and operating to emit a series of acoustic waveforms across a measuring area. In one form, the device includes a second acoustic array situated in a second, slanted sidewall of the measuring area and operating to receive an acoustic signal resulting from the emitted series of acoustic waveforms or to receive said acoustic signal and emit a second series of acoustic waveforms. A the processor measures a time between when a predefined portion of one of the series of acoustic waveforms was emitted and when a predefined portion of the received acoustic signal corresponding to the predefined portion of one of the series of acoustic waveforms is received by the acoustic receiver, and correlates the measured time to a reference time, then outputs a correlation factor for determining the velocity of sound in the medium in the measuring area. The processor may also calculate transit time for the two emitted acoustic signals or echoes from the first emitted acoustic signals to determine medium flow velocity.

26 Claims, 6 Drawing Sheets

(56) References Cited

U.S. PATENT DOCUMENTS

| | | |
|---|---|---|
| 5,467,320 A | 11/1995 | Maki, Jr. |
| 5,475,650 A * | 12/1995 | Sinha et al. ............ 367/31 |
| 5,874,676 A | 2/1999 | Maki, Jr. |
| 5,992,223 A | 11/1999 | Maki, Jr. |
| 6,098,021 A * | 8/2000 | Tang et al. ............ 702/14 |
| 6,189,383 B1 | 2/2001 | Tello et al. |
| 6,538,958 B1 | 3/2003 | Blankinship et al. |
| 6,829,947 B2 | 12/2004 | Han et al. |
| 6,988,566 B2 * | 1/2006 | Lockerd et al. ............ 175/45 |
| 7,197,942 B2 * | 4/2007 | Gysling et al. ............ 73/861.23 |
| 7,418,865 B2 | 9/2008 | Griffiths et al. |
| 8,559,272 B2 * | 10/2013 | Wang ............ 367/82 |
| 2004/0095847 A1 | 5/2004 | Hassan et al. |
| 2008/0186805 A1 | 8/2008 | Han |
| 2009/0173150 A1 | 7/2009 | DiFoggio et al. |
| 2009/0196120 A1 | 8/2009 | Geerits |
| 2010/0010351 A1 | 1/2010 | Jovanovic et al. |
| 2010/0315900 A1 | 12/2010 | DiFoggio et al. |

* cited by examiner

SYSTEM AND DEVICE FOR ACOUSTIC MEASURING IN A MEDIUM

FIELD OF THE INVENTION

The present invention relates to the field of acoustic measurement devices and, more particularly, to devices for acoustic measuring in a medium.

BACKGROUND

Within the drilling industry, LWD (Logging While Drilling) devices have used acoustic pulse-echo measurements to measure a variety of parameters of a bore hole such as standoff, caliper, imaging and the like. These devices have one or more acoustic transducers that emit an acoustic pulse toward a surface being probed and then receive a reflected signal. Time between when the acoustic pulse is emitted and when a reflected signal is received (acoustic transit time) can then be used in the determination of distance. When the velocity of sound in a medium is known, acoustic transit time can be used to determine exact distance between the acoustic transducer and the surface being probed. Because the acoustic transducer of these devices is positioned such that at least some if not all of the acoustic signal path propagates through a fluid medium in the bore hole (e.g. a liquid such as drilling mud or mud), inaccuracies are introduced into the value of the speed of sound in the fluid medium (known as the acoustic velocity of the medium). Inaccuracy in the measurement of acoustic velocity translates into inaccuracy in the determination of distance. In the context of a bore hole, presence of the drilling mud creates inaccuracies into the determination of distance given that the precise acoustic velocity of the mud is not known.

Because drilling mud is formulated to exhibit particular properties, each formulation has a unique acoustic velocity. In addition, during the drilling process the speed of sound in the mud is determined by factors other than its initial unique acoustic velocity such as mud type (oil or water), mud weight, mud density, mud temperature, mud pressure, the amount of cuttings in the mud, the amount of formation fluids entering the mud, and the like. Conditions change such that the acoustic velocity in the mud changes. Therefore, it is difficult to accurately determine acoustic velocity in a fluid medium within a bore hole during drilling.

Because many LWD bore hole measurements use acoustic velocity to determine distance, it is desirable during the drilling process to be able to accurately determine the acoustic velocity in a medium in a bore hole. Moreover, it is desirable to be able to accurately calibrate the various LWD measurements through accurate measurement of acoustic velocity in a medium in a bore hole during the drilling process. Moreover, it may be desirable to determine mud velocity or speed within the bore hole.

The problems in the prior art, the desirables presented above and more are addressed by the present invention.

SUMMARY OF THE INVENTION

The present invention is an acoustic measuring system, device and method for acoustic measuring in a medium, particularly but not necessarily, in a bore hole. The present acoustic measuring system, device and method are moreover adapted for acoustic measurement in a medium within other bounded spaces such as pipes, conduit, blood vessels and the like. Without being exhaustive, the present acoustic measuring system, device and method may be used to measure velocity of sound in a medium or to measure flow velocity of a medium within a bore hole.

In one form, an apparatus according to the principles of the present invention, comprises a measuring area, an acoustic transmitter situated relative to a first surface of the measuring area, an acoustic receiver situated relative to a second surface of the measuring area and non-parallel to the first surface, and a processor in communication with the acoustic transmitter and the acoustic receiver. At least one of the acoustic transmitter or the acoustic receiver has a plurality of acoustic elements, the acoustic transmitter is operable to emit a series of acoustic waveforms, and the acoustic receiver is operable to receive an acoustic signal that is a result of the series of acoustic waveforms. The processor is operable to measure a time between when a predefined portion of one of the series of acoustic waveforms was emitted and when a predefined portion of the received acoustic signal corresponding to the predefined portion of one of the series of acoustic waveforms is received by the acoustic receiver, correlate the measured time to a reference time of an acoustic waveform traveling in a known medium, the reference time corresponding to a velocity of sound in the known medium; and output a correlation factor which may be used to determine the velocity of sound in the medium in the measuring area.

In one form, a method according to the principles of the present invention, comprises providing a device having a measuring area, an acoustic transmitter situated in a first surface of the measuring area, the acoustic transmitter in communication with a processor, and an acoustic receiver situated in a second surface of the measuring area and non-parallel to the first surface, the acoustic receiver in communication with the processor, wherein at least one of the acoustic transmitter or the acoustic receiver has a plurality of acoustic elements, the acoustic transmitter is operable to emit a series of acoustic waveforms that result in one effective waveform in the media, and the acoustic receiver is operable to receive an acoustic signal that is a result of the unique individual acoustic waveforms from each element. The method including measuring via the processor, a time between when a predefined portion of one of the series of acoustic waveforms was emitted and when a predefined portion of the received acoustic signal corresponding to the predefined portion of one of the series of acoustic waveforms is received by the acoustic receiver, correlating via the processor, the measured time to a reference time of an acoustic waveform traveling in a known medium, the reference time corresponding to a velocity of sound in the known medium, and outputting via the processor, a correlation factor which may be used to determine the velocity of sound in the medium in the measuring area.

In another form, an apparatus and method according to the principles of the present invention, comprises a measuring area, a first acoustic transducer array situated relative to a first surface of the measuring area, a second acoustic transducer array situated relative to a second surface of the measuring area and non-parallel to the first surface, and a processor in communication with the first and second acoustic transducer arrays. The first acoustic transducer array is operable to emit a series of acoustic waveforms in a direction of medium flow, while the second acoustic transducer array is operable to receive an acoustic signal that is a result of the series of acoustic waveforms emitted by the first acoustic transducer array. The processor is operable to measure a time between when a predefined portion of one of the series of acoustic waveforms was emitted by the first acoustic transducer array and when a predefined portion of the received acoustic signal corresponding to the predefined portion of one of the series of acoustic waveforms is received by the second acoustic transducer array. The second acoustic transducer array is operable to emit a series of acoustic waveforms in a direction opposite of medium flow, while the first acoustic transducer array is operable to receive an acoustic signal that is a result of the series of acoustic waveforms emitted by the second acoustic transducer array. The processor is operable to measure the time between when a predefined portion of one of the series of acoustic waveforms was emitted by the second acoustic transducer array and when a predefined portion of the received acoustic signal corresponding to the predefined portion of one of the series of acoustic waveforms is received by the first acoustic transducer array, and calculate medium flow speed or velocity based on the measured travel times of the two emitted acoustic waveforms.

In another form of an apparatus and method according to the principles of the present invention, comprises a measuring area, an acoustic transducer array situated relative to a first slanted surface of the measuring area, and a processor in communication with the acoustic transducer array. The acoustic transducer array is operable to emit a series of acoustic waveforms in a direction of medium flow and to receive an acoustic signal that is a result of echoes from particulates in the medium. The processor operable to calculate frequency shift of the returned acoustic signal.

DETAILED DESCRIPTION

Figure 1:
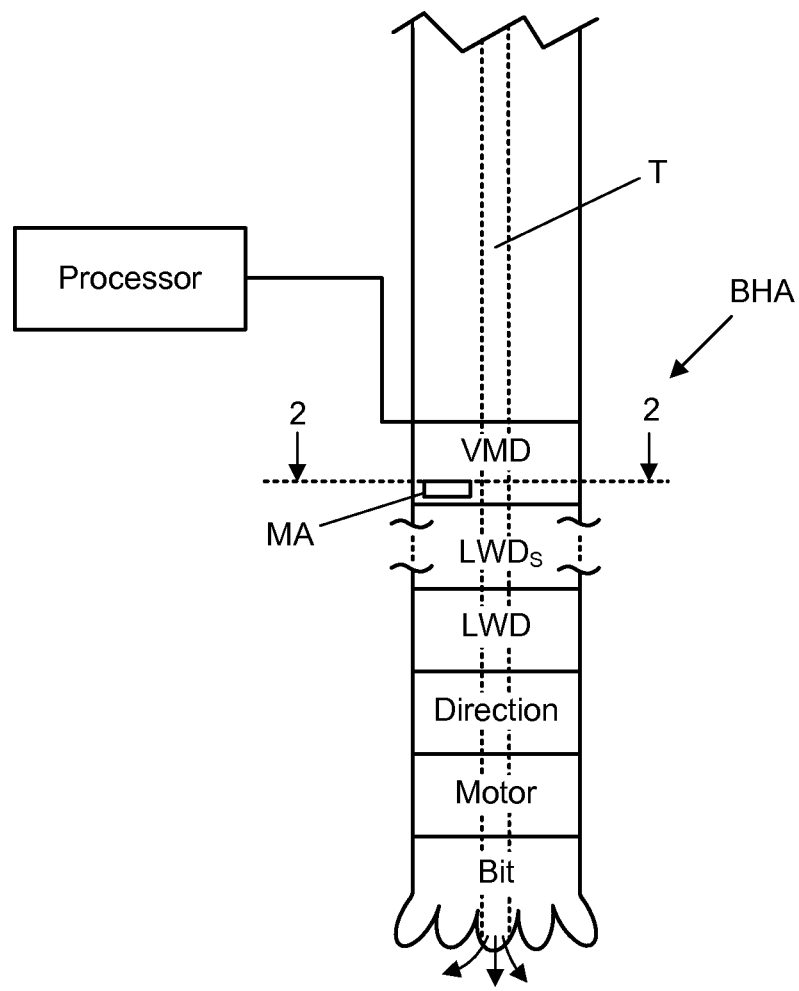
FIG. 1 illustrates an exemplary Bottom Hole Assembly (BHA) for a drilling operation having or incorporating the present velocity measuring device or tool (VMD) as provided herein.

FIG. 1 illustrates an exemplary Bottom Hole Assembly (BHA) for a drilling operation having or incorporating the present velocity measuring device or tool (VMD) as provided herein. The BHA has a typical drill bit, motor, direction tool, one or more LWDs, and the present VMD. The components of the BHA, like the drilling pipe itself, are cylindrical, hollow, and threaded one each end in order to mount with pipe or BHA component (e.g. LWD, VMD or Direction), the outer diameter of the BHA components being less than that of the drill bit. Drilling mud is introduced through a tube or conduit T that extends from the surface of the bore hole to the BHA, with the tube T formed through the BHA components by their respective hollows. The drilling mud exits the tube T via the drill bit such that the mud flows around the drill bit, into and circulates upward through the bore hole (as represented by the arrows emanating from the end of drill bit) towards the surface of the bore hole. It should be appreciated that the VMD and/or other BHA components other than the drill bit may be rotated during drilling or held stationary while the drill bit rotates.

A Processor is in communication with the VMD as well as other BHA components (e.g. LWDs). The Processor may be incorporated into the VMD or may separate from the VMD. When separate, the Processor may be a stand alone device (e.g. a computer), as part of another BHA component or otherwise. In all cases, the Processor is configured and operable to perform the functions and features described herein.

Figure 2:
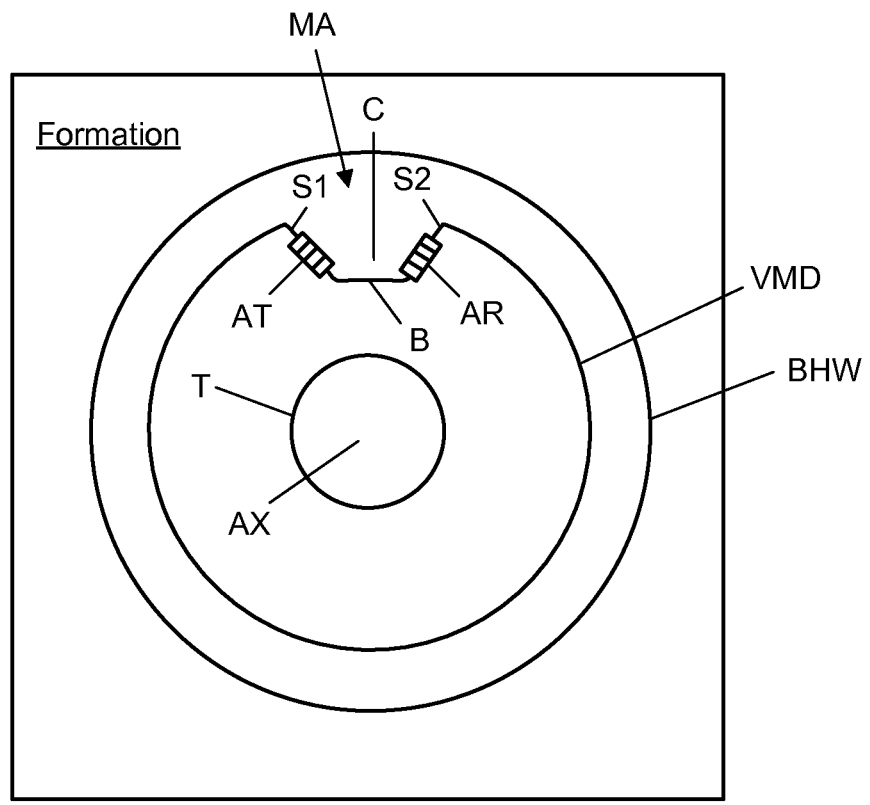
FIG. 2 depicts an azimuthal cross section of the velocity measuring device or tool VMD, the VMD surrounded by a bore hole wall BHW of a bore hole in a Formation.

A measuring area MA is provided in a face or surface of the measuring tool, the measuring area MA defined by a concavity, chamber, depression, hollow, recess, notch, indention or the like. FIG. 2 depicts an azimuthal cross section of the velocity measuring device or tool VMD, the VMD surrounded by a bore hole wall BHW of a bore hole in a Formation. The VMD may rotate about the axis of rotation AX. FIG. 2 particularly shows an exemplary embodiment of a measuring area MA disposed in the cylindrical surface of the VMD. The measuring area MA extends a depth into the tool and defines a bottom B with first and second sides, surfaces or side surfaces S1 and S1, it being understood that the nomenclature first and second is arbitrary. The bottom B is preferably, but not necessarily, rounded rather than squared in the azimuthal direction in order to achieve better flow characteristics within the notch thereby alleviating and/or preventing clogging. The lateral walls of the measuring area MA are rounded as well.

It should be appreciated that care be taken to avoid making the depth of the measuring area MA too deep. Any cut in the tool weakens the structural integrity of the tool especially if the tool is used rotating in a deviated or non-linear bore hole. Large cuts in the tool greatly weaken the tool. Large cuts in the tool can also collect debris which may interfere with an accurate measurement. The measuring area MA thus has to be a very gentle profile.

Rather than being perpendicular (a vertical at 90°) to the bottom B of the measuring area MA, the first side S1 angles away from the vertical (outwardly) in a counterclockwise direction as viewed in FIG. 2, while the second side S2 angles from the vertical (outwardly) in a clockwise direction as viewed in FIG. 2, such that the sides S1, S2 are non-parallel. The angle (□) of each side S1, S2 relative to the vertical is preferably, but not necessarily, the same. While the angle of a side S1, S2 may vary from the vertical, the angle must not be so great such that sound emanating from the acoustic transmitter/transducer (AT) does not reflect off the bore hole wall BHW. Thus it is preferable that the angle of the sides be between 15° and 35°. In FIG. 2, the first side S1 is angled approximately 20° from the vertical (90°) in the counterclockwise direction while the second side is angled approximately 20° from the vertical in the clockwise direction. Because the angles of the sides S1, S2 is known, the distance between the two sides S1, S2 is now known (see D of FIG. 3). Distance is now controlled and is no longer an unknown.

As indicated, an acoustic transmitter or transducer AT is provided on, in, into or relative to the side or surface S1 and an acoustic receiver or transducer AR is provided on, in, into or relative to the side or surface S2. While various types of acoustic transmitters and receivers may be used, the present invention contemplates and preferably, but not necessarily, uses ultrasonic transmitters/receivers (transducers) such as piezoelectric transmitters/receivers (transducers).

In one form, the acoustic transmitter AT is formed of a plurality of acoustic transmitting elements (an acoustic transmitting array) and the acoustic receiver AR is formed of a plurality of acoustic receiving elements (an acoustic receiving array). In another form, the acoustic transmitter AT is formed of a plurality of acoustic transmitting elements (an acoustic transmitting array) and the acoustic receiver is formed of a single receiver/receiving element. In a further form, the acoustic transmitter AT is formed of a single transmitter/transmitting element and the acoustic receiver AR is formed of a plurality of acoustic receiving elements (an acoustic receiver array). Thus, one or both of the acoustic transmitter AT and the acoustic receiver AR consists of an array of acoustic elements. It is preferable, however, that the sound velocity measuring device uses an acoustic transmitting array (ATA) and an acoustic receiving array (ARA). This configuration is depicted in FIG. 3 in which is shown a velocity measuring device (VMD) fashioned in accordance with the present principles.

While the acoustic transmitting array ATA of the velocity measuring device VMD is shown having four (4) acoustic transmitting elements (ate), it should be appreciated that the acoustic transmitting array ATA may have from two (2) to any number of acoustic transmitting elements as is practical. Similarly, while the acoustic receiving array ARA of the velocity measuring device VMD is shown having four (4) acoustic transmitting receivers (atr), it should be appreciated that the acoustic receiving array ARA may have from two (2) to any number of acoustic receiving elements (are) as is practical.

Figure 3:
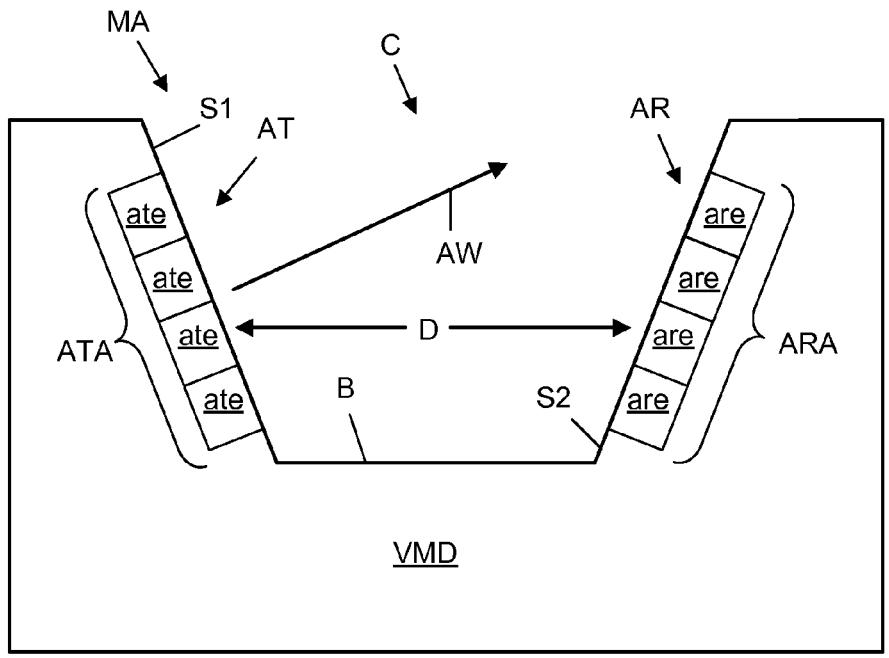
FIG. 3 shows a velocity measuring device in accordance with the principles of the present invention with the acoustic transmitter AT thereof emitting an acoustic waveform AW for reception by the acoustic receiver AR thereof.

The velocity measuring device VMD of FIG. 3 depicts the acoustic transmitter AT emitting an acoustic waveform AW for reception by the acoustic receiver AR. The acoustic waveform AW is the result of a series of acoustic waveforms transmitted by the acoustic transmitter. An exemplary acoustic waveform of the series of acoustic waveforms is provided in FIG. 4. It is evident that numerous combinations of acoustic transmissions from the various acoustic transmitting elements of the acoustic transmitting array may create the acoustic waveform AW. The present velocity measuring device, however, preferably transmits a series of acoustic waveforms from the acoustic transmitter AT. For each measurement or generation of acoustic waveform AW, each acoustic transmitting element emits a single waveform (e.g. a pulse). The individual waveforms from each acoustic transmitting element form the single acoustic waveform in the medium. In the case of single acoustic transmitting element, individual waveforms (e.g. pulses) must be emitted serially. Any resulting acoustic waveform is received by each one of the acoustic receiving elements in the case of an array of acoustic receiving elements or by a single acoustic receiving element.

Figure 4:
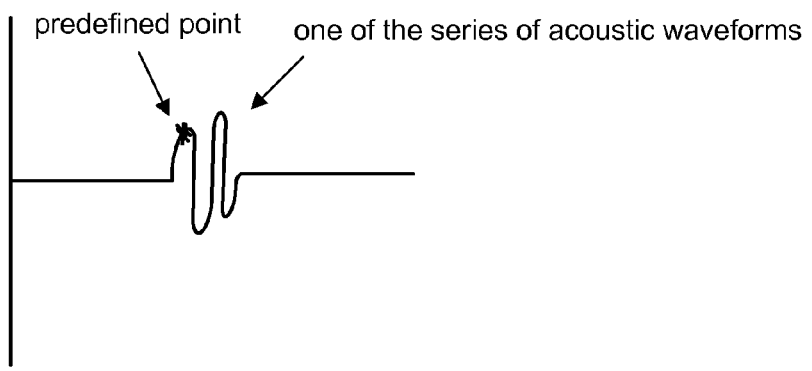
FIG. 4 shows a predefined point represented by an asterisk on the waveform.

A portion or feature of an emitted acoustic waveform of the series of acoustic waveforms is selected. This predefined point is represented in FIG. 4 by an asterisk on the waveform. The acoustic receiver receives and monitors the resulting waveform to detect a corresponding predefined point in the received waveform or signal. Time is measured between when a predefined point or portion of one of the series of acoustic waveforms is emitted and when a predefined point or portion of the received acoustic waveform or signal is received by the acoustic receiver.

Thereafter, the Processor correlates the measured time to a reference time of an acoustic waveform traveling in a known medium with the reference time corresponding to a velocity of sound in the known medium. The Processor provides a correlation factor that may be used to determine the velocity of sound in the medium in the measuring area. This is discussed further below.

In the preferred embodiment of the present invention, the acoustic transmitting array ARA provides an acoustic waveform from each acoustic transmitting element of the array sequentially, beginning from an upper acoustic transmitting element to a lower acoustic transmitting element, the nomenclature upper and lower with respect to the axis AX of the VMD.

Figure 5:
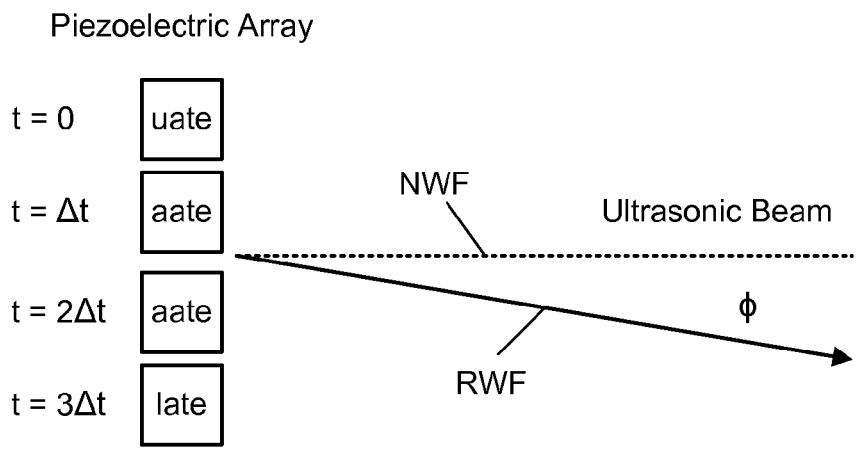
FIG. 5 illustrates the sequential firing of a piezoelectric array of the acoustic transmitter AT of the present velocity measuring device.

FIG. 5 illustrates the sequential firing of a piezoelectric array of the acoustic transmitter AT. The upper acoustic transmitting element (uate) fires first (t=0). The adjacently lower acoustic transmitting element (aate) fires second after a first time delay (t=$\Delta$t). The next adjacently lower acoustic transmitting element (aate) fires third after a second time delay (t=2$\Delta$t). The last or lower acoustic transmitting element (late) fires last after a third time delay (t=3$\Delta$t).

A single or concerted ultrasonic waveform (NWF) would have a wave or beam front defining a plane of propagation co-planar with the piezoelectric array of the acoustic transmitter and traveling along a path represented by the normal dashed line of FIG. 5. However, since the individual acoustic transmitting elements of the array are fired sequentially from the top or upper acoustic transmitting element to the bottom or lower acoustic transmitting element with the time delays as indicated, the resulting waveform has a wave front (RWF) defining a plane of propagation that is bent from normal $\phi$ degrees but parallel to the channel bottom, wherein $\phi$ is determined by frequency (f) of the ultrasound and the time delay ($\Delta$t). Therefore, the plane of the resulting beam front can be bent or modified from normal as desired.

Figure 6:
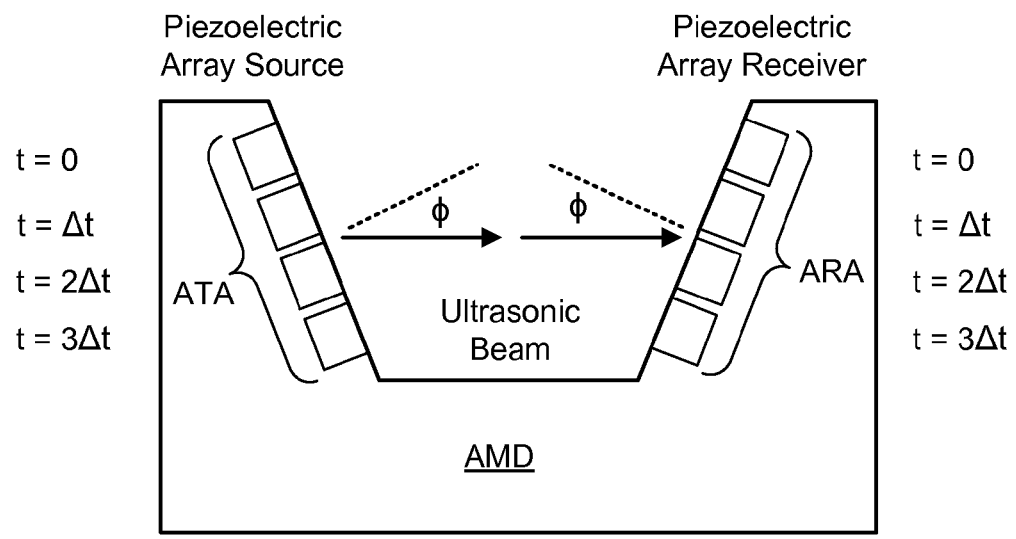
FIG. 6 shows an acoustic measuring device in accordance with the present principles illustrating the manner in which an acoustic signal is sent from the angled acoustic piezoelectric transmitting array ATA thereof and received by the acoustic piezoelectric receiving array ARA thereof.

As seen in FIG. 6, with the angled position of the acoustic piezoelectric transmitting array ATA and of the acoustic piezoelectric receiving array ARA the angle $\phi$ ($\angle\phi$) provides a resulting wave front with a wave front plane generally represented by the dark arrows (as opposed to the dashed line normal wave front). The resulting waveform is received by the acoustic receiving array. Particularly, each ultrasonic receiving element of the array receives the resulting waveform with time delays ($\Delta$t). Preferably, the ultrasonic sensitivity of the ultrasonic receiver array is bent by the angle $\phi$, the angle of beam arrival.

As indicated above, the piezoelectric array receives and monitors the resulting waveform to detect a corresponding predefined point in the received waveform or signal. Time is measured between when a predefined point or portion of the first ultrasonic waveform of the series of acoustic waveforms is emitted and when a predefined point or portion of the resulting waveform is received. This is accomplished for each receiver of the array, with the corresponding time delay added. An average of the measurements provides a measured time. Again, thereafter, the Processor correlates the measured time to a reference time of an acoustic waveform traveling in a known medium with the reference time corresponding to a velocity of sound in the known medium. The Processor provides a correlation factor that may be used to determine the velocity of sound in the medium in the measuring area.

In order to correlate the measured time to a reference time, the present velocity measure device must be calibrated to a known medium. The medium selected is typically water, since water is readily available and has well known properties including sound speed at various temperatures and pressures. This is good because measurements must be taken in multiple conditions for more accurate calibration. Dimensions of the measuring area are taken so that distance (D) between the transmitting array and the receiving array (or sides) of the measuring area is known.

For water of a given temperature and/or other characteristics, a measured transmit time is obtained. Since the transit distance is known, the speed or velocity of sound in water of the given temperature and/or other characteristics in the measuring area is determined with great accuracy. Speed of sound in water versus transit time may be generated from various calibration measurements. Obviously, for a given distance, the faster the transit time, the faster the speed of sound in the medium and vice versa. Therefore, a measured time in a medium can be compared or correlated to the transit time in the known medium (e.g. water) and a correlation factor can be provided which can then be used to calibrate other LWD tools/measurements.

As described above, the acoustic measuring device AMD of the present invention may be used to measure velocity of sound in a medium in a borehole, particularly, but not necessarily, of mud within a borehole. It should be appreciated however, that the present acoustic measuring device AMD may be used for other borehole measurements. For instance, the present acoustic measuring device AMD may be used to measure a rate at which a medium is flowing past the acoustic measuring device AMD (i.e. medium flow speed or velocity).

Figure 7:
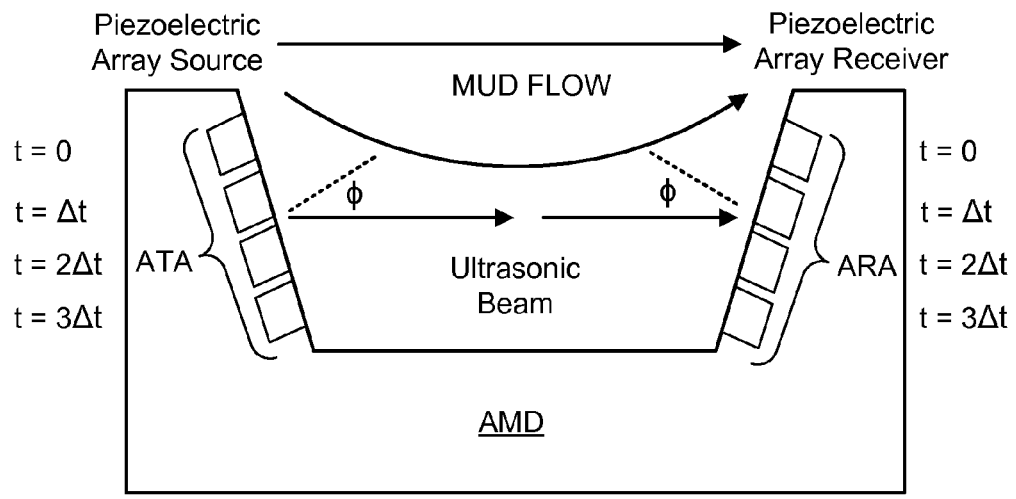
FIG. 7 shows an acoustic measuring device in accordance with the present principles illustrating a first part of a manner of measuring mud flow speed.
Figure 8:
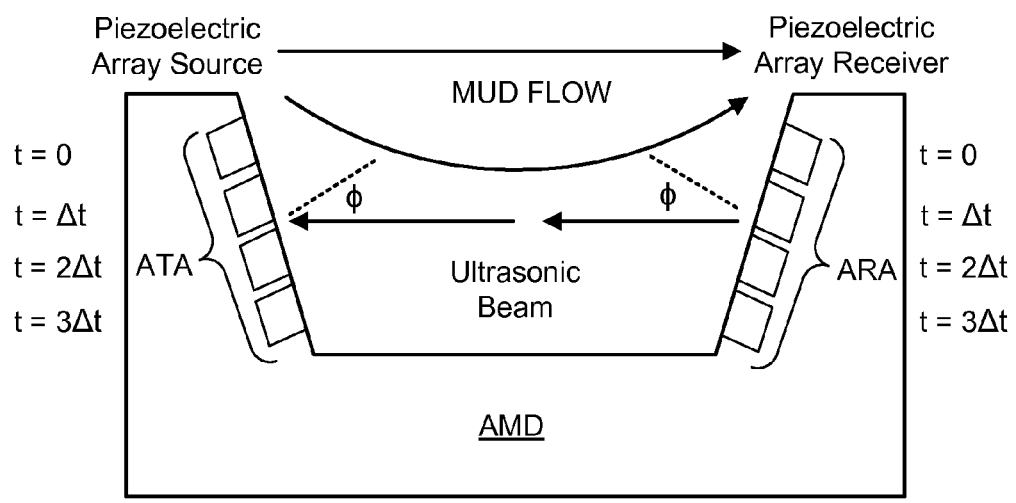
FIG. 8 shows the acoustic measuring device of FIG. 7 illustrating a second part of the manner of measuring mud flow speed.

Referring to FIGS. 7 and 8, a manner of measuring a rate at which a medium such as mud is flowing past the acoustic measuring device AMD (flow speed or velocity of the medium) is illustrated. In FIG. 7, mud flow is shown flowing past the acoustic measuring device AMD and particularly the measuring area MA of the acoustic measuring device AMD. An ultrasonic (acoustic) signal is emitted by each element of the acoustic transducer array ATA (the first transducer array) with the time delays as illustrated in the direction of medium flow. With the angled position of the first acoustic piezoelectric transducer array ATA and of the second acoustic piezoelectric transducer array ARA the angle φ (∠φ) provides a resulting wave front with a wave front plane generally represented by the dark arrows (as opposed to the dashed line normal wave front). The resulting waveform is received by the second acoustic transducer array ARA. Particularly, each ultrasonic receiving element of the array ARA receives the resulting waveform with time delays (Δt) as illustrated. Preferably, the ultrasonic sensitivity of the ultrasonic receiver array is bent by the angle φ, the angle of beam arrival. With a source-receiver separation D of the acoustic measuring device AMD, the processor determines a travel time $t_1$, wherein $t_1 = D/(V_{medium} + V_{vlow})$.

As depicted in FIG. 8, an ultrasonic (acoustic) signal is then emitted by each element of the second acoustic transducer array ARA with the time delays as illustrated in a direction opposite to medium flow. With the angled position of the second acoustic piezoelectric transducer array ARA and of the first acoustic piezoelectric transducer array ATA the angle φ (∠φ) provides a resulting wave front with a wave front plane generally represented by the dark arrows (as opposed to the dashed line normal wave front). The resulting waveform is received by the first acoustic transducer array ATA. Particularly, each ultrasonic receiving element of the array ATA receives the resulting waveform with time delays (Δt) as illustrated. Preferably, the ultrasonic sensitivity of the ultrasonic receiver array is bent by the angle φ, the angle of beam arrival. With a source-receiver separation D of the acoustic measuring device AMD, the processor determines a travel time $t_2$, wherein $t_2 = D/(V_{medium} + V_{vlow})$.

The flow velocity or speed of the medium is then calculated by the processor via the equation $V_{flow} = (t_1 - t_2)/D$. This may be described as an "upstream and downstream" or "pitch-catch". Support for this manner of flow rate measurement is described in U.S. Pat. No. 4,905,203 issued to Sims et al. on Feb. 27, 1990, and in U.S. Pat. No. 4,452,007 issued to Siegfried, II on Jun. 5, 1984, the entire contents of both of which are incorporated herein by reference. These patents, however, do not utilize the present acoustic measuring device AMD to obtain such measurement. It should also be appreciated that this measurement method may be accomplished using a first single transducer instead of a first transducer array, and a second single transducer instead of a second transducer array.

Figure 9:
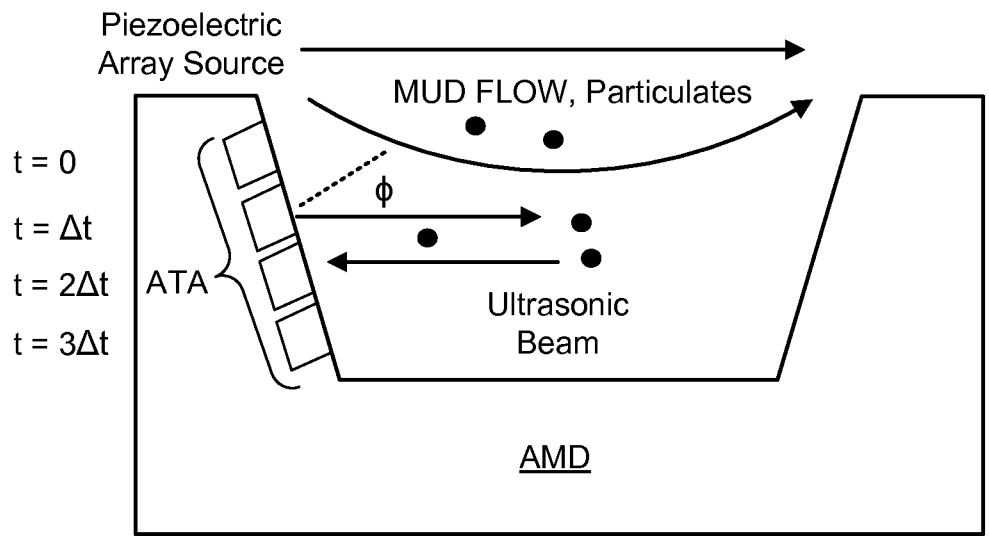
FIG. 9 shows an acoustic measuring device in accordance with the present principles illustrating a further manner of measuring mud flow speed.

Referring to FIG. 9, another manner of measuring a rate at which a medium (e.g. mud) is flowing past the acoustic measuring device AMD is illustrated. In this method, frequency shift (i.e. Doppler Shift) is used to determine medium flow velocity. The acoustic measuring device AMD of this embodiment utilizes a single acoustic transducer array ATA that transmits and receives acoustic waveforms. Alternatively, the single acoustic transducer may be a single transducer rather than a transducer array. In the case of a transducer array, an acoustic waveform is continuously emitted from each element of the acoustic array at the various delays indicated in FIG. 9. In the case of a single transducer, an acoustic waveform is continuously emitted from the single transducer. In both cases, acoustic echoes (signals) from particulates in the medium are received by the transducer. Return energy of the echo(es) is measured. The processor calculates frequency shift of the returned acoustic signal to determine particulate/medium (mud) flow rate. Particularly, particulate/mud flow rate $V_{particulate}/V_{mud} = \Delta f/f$. Measurement may be accomplished either while rotating or stationary.

Support for this manner of flow rate measurement is described in U.S. Pat. No. 4,982,383 issued to Sims et al. on Jan. 1, 1991, the entire contents of which is incorporated herein by reference. This patent, however, does not utilize the present acoustic measuring device AMD to obtain such measurement.

While the invention has been illustrated and described in detail in the drawings and foregoing description, the same is to be considered as illustrative and not restrictive in character and that all changes and modifications that come within the spirit of the invention are desired to be protected.

All references cited in this specification are incorporated herein by reference to the extent that they supplement, explain, provide a background for or teach methodology or techniques employed herein.

What is claimed is:

1. An acoustic measuring device of a medium in a borehole, the acoustic measuring device comprising:
   a measuring area;
   an acoustic transmitter situated in a first surface of the measuring area;
   an acoustic receiver situated in a second surface of the measuring area and non-parallel to the first surface; and
   a processor in communication with the acoustic transmitter and the acoustic receiver;
   at least one of the acoustic transmitter or the acoustic receiver having a plurality of acoustic elements;
   the acoustic transmitter operable to emit a series of acoustic waveforms;

the acoustic receiver operable to receive an acoustic signal that is a result of the emitted series of acoustic waveforms;

the processor operable to: measure a time between when a predefined portion of one of the series of acoustic waveforms was emitted and when a predefined portion of the received acoustic signal corresponding to the predefined portion of one of the series of acoustic waveforms is received by the acoustic receiver;

correlate the measured time to a reference time of an acoustic waveform traveling in a known medium, the reference time corresponding to a velocity of sound in the known medium; and output a correlation factor used to provide a determination of a velocity of sound in a medium in the measuring area.

2. The acoustic measuring device of claim 1, wherein the acoustic transmitter and the acoustic receiver comprise ultrasonic piezoelectric elements.

3. The acoustic measuring device of claim 1, wherein the measuring area is concave.

4. The acoustic measuring device of claim 3, wherein the concave measuring area is defined by an arced rear surface that extends from an upper area of a face of the device to a lower area of the face of the device, the first surface of the measuring area angled inwardly from the face into and intersecting with the arced rear surface, and the second surface of the measuring area angled inwardly from the face into and intersecting with the arced rear surface.

5. The acoustic measuring device of claim 1, wherein the acoustic transmitter has a plurality of acoustic transmitting elements and the acoustic receiver has a plurality of acoustic receiving elements.

6. The acoustic measuring device of claim 5, wherein the number of the plurality of acoustic receiving elements equals the number of the plurality of acoustic transmitting elements.

7. The acoustic measuring device of claim 5, wherein the number of acoustic transmitting elements is at least four and the number of acoustic receiving elements is at least four.

8. The acoustic measuring device of claim 5, wherein each acoustic transmitting element of the plurality of acoustic transmitting elements emits one acoustic waveform of the emitted series of acoustic waveforms.

9. The acoustic measuring device of claim 8, wherein the plurality of acoustic waveforms are emitted sequentially from the plurality of acoustic transmitting elements beginning from an end acoustic transmitting element of the plurality of acoustic transmitting elements.

10. The acoustic measuring device of claim 5, wherein each acoustic receiving element of the acoustic receiver is operable to receive the acoustic signal that is a result of the series of acoustic waveforms, and the processor is operable to:

for each acoustic receiving element, measure a time between when a predefined portion of a first one of the series of acoustic waveforms was emitted and when a predefined portion of the received acoustic signal corresponding to the predefined portion of the first one of the series of acoustic waveforms is received;

correlate each measured time to a reference time of an acoustic waveform traveling in a known medium, the reference time corresponding to a velocity of sound in the known medium; and output a correlation factor which may be used to determine the velocity of sound in the medium in the measuring area.

11. A method for measuring velocity of sound in a medium in a borehole, the method comprising:

providing a device having:
a measuring area;
an acoustic transmitter situated in a first surface of the measuring area, the acoustic transmitter in communication with a processor; and
an acoustic receiver situated in a second surface of the measuring area and non-parallel to the first surface, the acoustic receiver in communication with the processor at least one of the acoustic transmitter or the acoustic receiver having a plurality of acoustic elements;
the acoustic transmitter operable to emit a series of acoustic waveforms;
the acoustic receiver operable to receive an acoustic signal that is a result of the series of acoustic waveforms;
measuring via the processor, a time between when a predefined portion of one of the series of acoustic waveforms was emitted and when a predefined portion of the received acoustic signal corresponding to the predefined portion of one of the series of acoustic waveforms is received by the acoustic receiver;
correlating via the processor, the measured time to a reference time of an acoustic waveform traveling in a known medium, the reference time corresponding to a velocity of sound in the known medium; and
outputting via the processor, a correlation factor which may be is used to determine the velocity of sound in the medium in the measuring area.

12. The method of claim 11, wherein the acoustic transmitter and the acoustic receiver comprise ultrasonic piezoelectric elements.

13. The method of claim 11, wherein the measuring area is concave.

14. The method of claim 13, wherein the concave measuring area is defined by an arced rear surface that extends from an upper area of a face of the device to a lower area of the face of the device, the first surface of the measuring area angled inwardly from the face into and intersecting with the arced rear surface, and the second surface of the measuring area angled inwardly from the face into and intersecting with the arced rear surface.

15. The method of claim 11, wherein the acoustic transmitter has a plurality of acoustic transmitting elements and the acoustic receiver has a plurality of acoustic receiving elements.

16. The method of claim 15, wherein the number of the plurality of acoustic receiving elements equals the number of the plurality of acoustic transmitting elements.

17. The method of claim 15, wherein the number of acoustic transmitting elements is at least four and the number of acoustic receiving elements is at least four.

18. The method of claim 15, wherein each acoustic transmitting element of the plurality of acoustic transmitting elements emits one acoustic waveform of the series of acoustic waveforms.

19. The method of claim 18, wherein the plurality of acoustic waveforms are emitted sequentially from the plurality of acoustic transmitting elements beginning from an end acoustic transmitting element of the plurality of acoustic transmitting elements.

20. The method of claim 15, wherein:
each acoustic receiving element of the acoustic receiver is operable to receive the acoustic signal that is a result of the series of acoustic waveforms; and
the method further comprises:

measuring for each acoustic receiving element via the processor, a time between when a predefined portion of a first one of the series of acoustic waveforms was emitted and when a predefined portion of the received acoustic signal corresponding to the predefined portion of the first one of the series of acoustic waveforms is received;

correlating each measured time via the processor, to a reference time of an acoustic waveform traveling in a known medium, the reference time corresponding to a velocity of sound in the known medium; and outputting a correlation factor which may be used to determine the velocity of sound in the medium in the measuring area.

21. An acoustic measuring device of a medium within an at least partially bounded space, the acoustic measuring device comprising:

a measuring area;

an acoustic transmitter situated in a first surface of the measuring area;

an acoustic receiver situated in a second surface of the measuring area and non-parallel to the first surface; and a processor in communication with the acoustic transmitter and the acoustic receiver;

at least one of the acoustic transmitter or the acoustic receiver having a plurality of acoustic elements;

the acoustic transmitter operable to emit a series of acoustic waveforms;

the acoustic receiver operable to receive an acoustic signal that is a result of the emitted series of acoustic waveforms;

the processor operable to:

measure a time between when a predefined portion of one of the series of acoustic waveforms was emitted and when a predefined portion of the received acoustic signal corresponding to the predefined portion of one of the series of acoustic waveforms is received by the acoustic receiver;

correlate the measured time to a reference time of an acoustic waveform traveling in a known medium, the reference time corresponding to a velocity of sound in the known medium; and output a correlation factor that is used to provide a determination of a velocity of sound in the medium within the at least partially bounded space.

22. A method for measuring velocity of sound in a medium within an at least partially bounded space, the method comprising:

providing a device having:

a measuring area;

an acoustic transmitter situated in a first surface of the measuring area, the acoustic transmitter in communication with a processor; and an acoustic receiver situated in a second surface of the measuring area and non-parallel to the first surface, the acoustic receiver in communication with the processor at least one of the acoustic transmitter or the acoustic receiver having a plurality of acoustic elements;

the acoustic transmitter operable to emit a series of acoustic waveforms;

the acoustic receiver operable to receive an acoustic signal that is a result of the series of acoustic waveforms;

measuring via the processor, a time between when a predefined portion of one of the series of acoustic waveforms was emitted and when a predefined portion of the received acoustic signal corresponding to the predefined portion of one of the series of acoustic waveforms is received by the acoustic receiver;

correlating via the processor, the measured time to a reference time of an acoustic waveform traveling in a known medium, the reference time corresponding to a velocity of sound in the known medium; and outputting via the processor, a correlation factor which is used to determine the velocity of sound in the medium in the measuring area.

23. An acoustic measuring device of a medium in a borehole, the acoustic measuring device comprising:

a measuring area;

a first acoustic transducer situated in a first surface of the measuring area;

a second acoustic transducer situated in a second surface of the measuring area and non-parallel to the first surface; and a processor in communication with the first and second acoustic transducers;

the first acoustic transducer operable to emit a first series of acoustic waveforms in a direction of medium flow;

the second acoustic transducer operable to receive an acoustic signal that is a result of the emitted first series of acoustic waveforms;

the processor operable to calculate a first transit time based on the acoustic signal that is a result of the emitted first series of acoustic waveforms;

the second acoustic transducer operable to emit a second series of acoustic waveforms in a direction opposite medium flow;

the first acoustic transducer operable to receive an acoustic signal that is a result of the emitted second series of acoustic waveforms;

the processor operable to calculate a second transit time based on the acoustic signal that is a result of the emitted second series of acoustic waveforms; and the processor providing a determination of velocity of the medium by use of the first and second calculated transit times.

24. The acoustic measuring device of claim 23, wherein the first and second acoustic transducers comprise transducer arrays.

25. An acoustic measuring device of a medium in a borehole, the acoustic measuring device comprising:

a measuring area;

an acoustic transducer situated in a first, slanted surface of the measuring area; and a processor in communication with the acoustic transducer;

the acoustic transducer operable to emit an acoustic waveform of a first frequency in a direction of medium flow and to receive a return acoustic waveform reflected from particulates in a medium in a borehole of a second frequency; and the processor operable to provide a determination of flow velocity of the medium by calculating a change between the first and second frequencies.

26. The acoustic measuring device of claim 25, wherein the acoustic transducer comprises a transducer array.

* * * * *